United States Patent [19]

Parten

[11] Patent Number: 6,150,553
[45] Date of Patent: Nov. 21, 2000

[54] METHOD FOR RECOVERING METHYL ACETATE AND RESIDUAL ACETIC ACID IN THE PRODUCTION ACID OF PURE TEREPHTHALIC ACID

[75] Inventor: William David Parten, Stockton on Tees, United Kingdom

[73] Assignee: E. I. du Pont de Nemours and Company, Wilmington, Del.

[21] Appl. No.: 09/257,275

[22] Filed: Feb. 24, 1999

Related U.S. Application Data

[63] Continuation-in-part of application No. 09/132,297, Aug. 11, 1998.

[51] Int. Cl.$^7$ .................................................. C07C 67/48
[52] U.S. Cl. ......................... 560/248; 562/608; 562/414
[58] Field of Search ............................ 560/248; 562/608, 562/414

[56] References Cited

U.S. PATENT DOCUMENTS

| | | |
|---|---|---|
| 1,860,512 | 5/1932 | Ricard et al. . |
| 1,917,391 | 7/1933 | Othmer . |
| 2,050,234 | 8/1936 | Othmer ................................ 260/122 |
| 2,050,235 | 8/1936 | Othmer ................................ 260/122 |
| 2,317,758 | 4/1943 | Guinot ................................. 202/42 |
| 2,395,010 | 2/1946 | Othmer ................................. 260/541 |
| 2,667,502 | 1/1954 | Steitz et al. ........................... 260/450 |
| 2,801,265 | 7/1957 | Coutor ................................. 260/541 |
| 3,052,610 | 9/1962 | Akaboshi et al. ....................... 202/42 |
| 3,394,058 | 7/1968 | Hohenschutz .......................... 203/60 |
| 3,844,903 | 10/1974 | Willersinn et al. ..................... 203/51 |
| 4,204,915 | 5/1980 | Kurata et al. .......................... 203/2 |
| 4,250,330 | 2/1981 | Costantini et al. .................... 562/409 |

FOREIGN PATENT DOCUMENTS

| | | |
|---|---|---|
| 9105989 | 8/1991 | Rep. of Korea . |
| 273744 | 11/1928 | United Kingdom . |
| 298137 | 9/1929 | United Kingdom . |
| 788931 | 1/1958 | United Kingdom . |
| 1039934 | 8/1966 | United Kingdom ............ C07C 54/42 |
| 1576787 | 10/1980 | United Kingdom ............. B01D 3/42 |
| 1593117 | 7/1981 | United Kingdom .......... C07C 51/265 |

OTHER PUBLICATIONS

Othmer, D. F., Azeotropic separation, *Chemical Engineering Progress*, 59, No. 6, 67–78, Jun. 1963.

*Primary Examiner*—Samuel Barts
*Attorney, Agent, or Firm*—Charles E. Krukiel

[57] ABSTRACT

A method for recovering methyl acetate and residual acetic acid in a two-stage process for producing pure terephthalic acid having a first oxidation stage and a second purification stage.

4 Claims, 2 Drawing Sheets

METHOD FOR RECOVERING METHYL ACETATE AND RESIDUAL ACETIC ACID IN THE PRODUCTION ACID OF PURE TEREPHTHALIC ACID

This application is a continuation-in-part of application Ser. No. 09/132,297, filed Aug. 11, 1998.

BACKGROUND OF THE INVENTION

The present invention relates to a two-stage process for producing pure terephthalic acid according to a first oxidation stage and a second purification stage, and, more particularly, to a method for recovering methyl acetate and residual acetic acid in such two-stage process.

Terephthalic acid is produced on a commercial scale by oxidation of paraxylene in the presence of a metal bromide catalyst system in acetic acid solvent. A crude, i.e., impure, terephthalic acid product is isolated from a slurry in the oxidation stage, usually as a dry crystalline powder. The crude terephthalic acid in the form of a wet cake is washed as necessary with acetic acid or water and is then sent to a dryer where any adherent solvent is removed to form crude terephthalic acid. Water is produced in a reaction off-gas stream as a significant by-product of the oxidation reaction. The off-gas stream also includes acetic acid and low levels of methyl acetate. A preferred means for separating and recovering the acetic acid from the off-gas stream is through azeotropic distillation of the off-gas stream condensate using an organic entrainer selected from, for example, n-butyl acetate, n-propyl acetate and isobutyl acetate. In such cases where the main feed to the azeotropic distillation process is derived from the oxidation reaction overheads, the presence of methyl acetate in the feed stream can adversely affect the amount of water which can be removed azeotropically because methyl acetate's water azeotrope lies in the single phase region, i.e. its water azeotrope will have a low water content.

In the second, i.e., purification, stage of the process, crude terephthalic acid crystals are dissolved in water at elevated pressure and temperature and the solution is subjected to hydrogenation in the presence of a Group VIII noble metal hydrogenation catalyst. The purified acid is recovered by crystallizing the acid from the hydrogen treated aqueous solution. A majority of the principal impurities, which are p-toluic acid derived from the compound 4-carboxybenzaldehyde and unidentified color bodies, along with some other organic components, such as benzoic acid and residual terephthalic acid, remain dissolved in the aqueous solution. This remaining aqueous solution is referred to hereinafter as "pure plant mother liquor", i.e., PPML. More recent commercial two-stage processes, however, have sought to eliminate the need to recover the crude terephthalic acid as a dry product with a separate drying step. Instead, the terephthalic acid crystals can be separated from the slurry formed in the oxidation stage by depositing the slurry on a moving band of filter material to form a wet cake and then washing the wet cake with water or other solvent according to a predetermined series of washing steps. The resulting wet cake can then be dissolved in water for purification without the need for a separate drying step.

For improved economy, it is desirable to recover and recycle the resulting pure plant mother liquor. However, under some process operating conditions, a residual amount of acetic acid can "slip" through the filtration/solvent exchange process, i.e., residual amounts retained within the recovered crude acid, and find its way into the aqueous mother liquor solution. The presence of acetic acid in the pure plant mother liquor can be problematic in attempting to recycle it for use elsewhere in the process. Hence, a method is needed to recover or otherwise account for the presence of a residual amount of acetic acid in the pure plant mother liquor.

SUMMARY OF THE INVENTION

The present invention is a method for recovering methyl acetate and residual acetic acid in a two-stage process for producing pure terephthalic acid. The two-stage process is characterized by a first oxidation stage and a second purification stage comprising the steps of:

(a) reacting paraxylene with air in the presence of acetic acid and a catalyst at elevated pressure and temperature to produce (1) an impure terephthalic acid which includes residual acetic acid and (2) a reaction off-gas stream comprising water, acetic acid and methyl acetate;

(b) cooling the reaction off-gas stream to form a first condensate and azeotropically dehydrating the first condensate in an azeotropic tower in the presence of an organic entrainer to produce a bottoms product comprising acetic acid and a tops product, and cooling the tops product to form a second condensate comprising water and methyl acetate as components of one phase and organic entrainer in another phase;

(c) purifying the crude terephthalic acid by dissolving it in water at elevated pressure and temperature to form an aqueous solution and contacting the aqueous solution with hydrogen in the presence of a catalyst;

(d) adjusting the pressure and temperature of the hydrogenated aqueous solution whereby pure terephthalic acid crystals precipitate and residual acetic acid and organic components remain in solution thereby forming pure plant mother liquor. The method of the invention comprises:

(e) simultaneously introducing the second condensate and the pure plant mother liquor into a decanter to thereby form an aqueous phase and an entrainer-rich organic phase wherein the residual acetic acid and the methyl acetate partition across both the aqueous phase and the entrainer-rich organic phase; and (f) returning the organic phase to the azeotropic tower to recover residual acetic acid and distilling the aqueous phase to recover methyl acetate.

In an alternate embodiment of the invention, the method comprises:

(a) separating the second condensate into an aqueous phase comprising water and residual acetic acid and an organic phase comprising entrainer;

(b) optionally preheating the organic phase comprising entrainer from step (a) and then simultaneously introducing the pure plant mother liquor and said organic phase into a decanter, optionally via a static mixer, to thereby form an aqueous phase and an entrainer-rich organic phase wherein the residual acetic acid and the methyl acetate partition across both the aqueous phase and the entrainer-rich organic phase; and (c) returning the organic phase to the azeotropic tower to recover residual acetic acid and distilling the aqueous phase to recover methyl acetate.

DETAILED DESCRIPTION OF THE INVENTION

Figure 1:
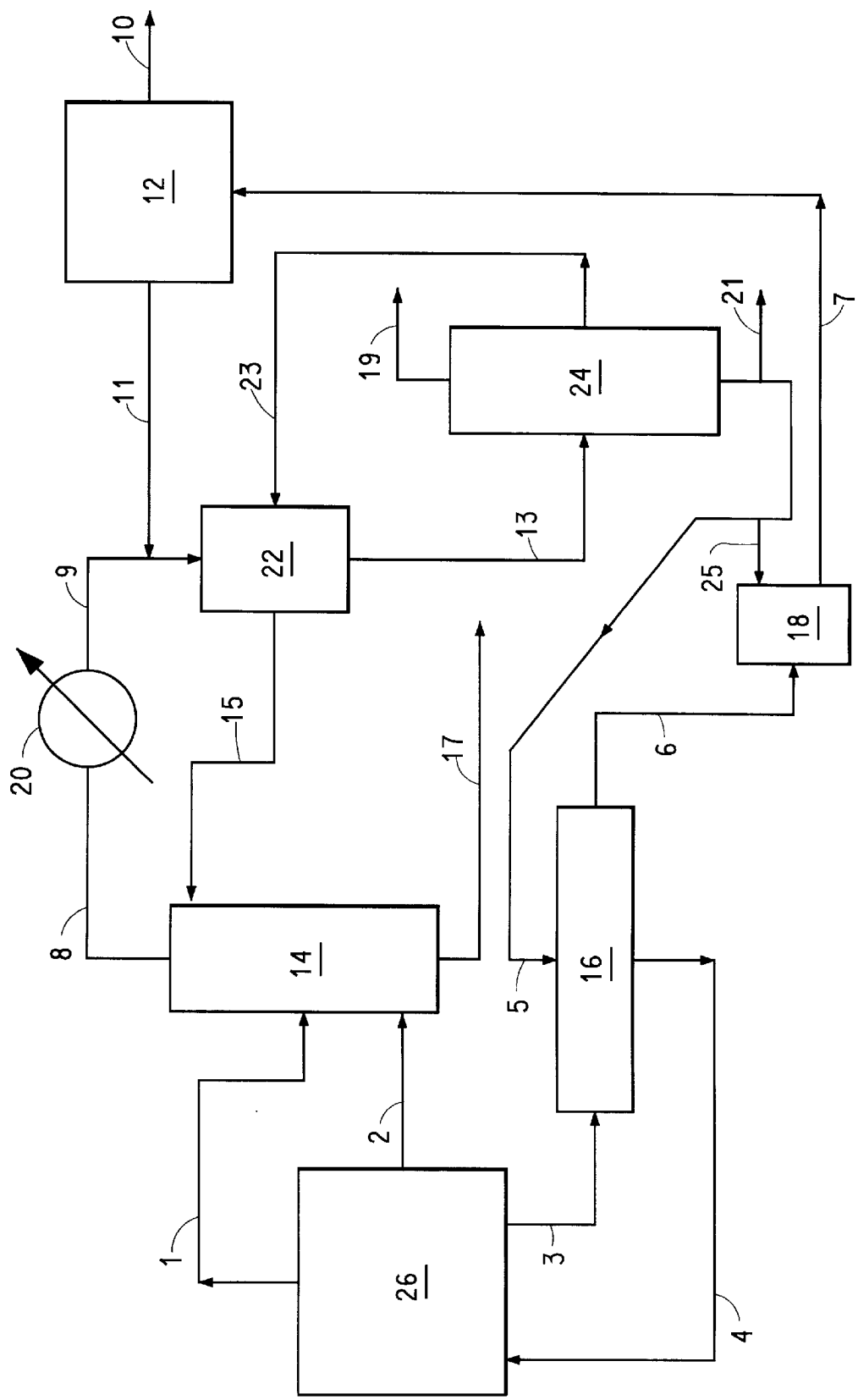
FIG. 1 is a schematic process diagram of one embodiment for carrying out the method of the invention.

The present invention provides for economic recovery of methyl acetate and residual amounts of acetic acid within a two-stage process for producing pure terephthalic acid. The first stage of a typical process involves the production of impure, i.e., crude, terephthalic acid by liquid phase air (molecular oxygen) oxidation of paraxylene in an aliphatic carboxylic acid solvent, such as acetic acid, using a heavy metal and bromine catalyst as described, for example, in Saffer et al. U.S. Pat. No. 2,833,816. The oxidation reaction is accomplished using a stirred reactor, and the reaction is accompanied by the production of an overhead vapor stream comprising water vapor, acetic acid and an amount of methyl acetate. The concentration of the components comprising the reactor overhead vapor stream can vary over a broad range, but typically the vapor stream will comprise in the range of 69% w/w acetic acid, 12% w/w water, 1% w/w methyl acetate with the balance being largely non-condensible components, such as nitrogen.

The overhead vapor stream is withdrawn from the reactor and cooled to form a first condensate. Some or all of this first condensate becomes a feed stream to an azeotropic distillation tower. Azeotropic distillation has proven to be an economical method for separating acetic acid from water wherein separation is accomplished in the presence of an organic entrainer selected from, for example, n-butyl acetate, n-propyl acetate and isobutyl acetate. Separation results in a bottoms product comprising around 95% by wt. acetic acid, which is recycled to the oxidation reaction, and a tops product comprising water, methyl acetate and organic entrainer. The tops product is, in turn, cooled, i.e., condensed, to form a second condensate which is separated into an organic phase and an aqueous phase. The organic phase is returned as reflux to the azeotropic tower and the aqueous phase is sent for treatment as an effluent. Methyl acetate tends to remain in the organic phase and will tend to interfere with the separation of acetic acid from water because its azeotrope has a low water content and lies in the single phase region. The present invention, therefore, is directed, in a first part, at recovering the methyl acetate.

The oxidation reaction yields a slurry of crude terephthalic acid crystals. The acid crystals can be recovered from the slurry by any suitable solvent exchange means, such as, for example, by centrifuge(s), rotary drum filter(s) or moving belt filter(s) arranged with re-slurry as appropriate for effective solvent interchange. Regardless of which method is employed, in practice, crude terephthalic acid crystals are recovered from the slurry, usually in the form of a wet cake, which is then washed at least once, but preferably several times in a series of washing steps, with either pure, i.e., fresh, water or water which has been recycled from some other part of the process. The wash water, which now contains a substantial amount of acetic acid solvent, can be recycled to the oxidation reaction. The recovered crude acid crystals, which can be either dried or in the form of a wet cake, are then dissolved in water to form a solution of the impure acid to begin the purification stage of the process.

Purification of the crude acid is accomplished by contacting the solution and hydrogen or a pre-humidified hydrogen-containing gas with a Group VIII Noble metal catalyst. Because of its low solubility, terephthalic acid requires either large volumes of water or high temperatures in order to obtain the desired terephthalic acid solution. In practice, the hydrogenation process can be conducted at a temperature within the range of from 200° C. up to the critical temperature of water, i.e., 374° C. Within the preferred temperature range, solutions of about 10% by wt. to about 35% by wt. terephthalic acid are used. Most of the impurities in the impure terephthalic acid are occluded in the acid crystals. By re-dissolving the crude crystals in water, the impurities are then in solution and subject to catalytic hydrogenation treatment.

Pressure conditions for the hydrogenation process depend upon the manner in which the process is conducted. Since the temperature of the solution is substantially above the boiling point of water, and since it is desirable to maintain the aqueous solution in liquid phase, the hydrogenation is carried out in a reactor at a pressure above atmospheric pressure, i.e., typically in the range of from 4000 kPa up to 20,000 kPa. The pressure level is selected to not only maintain the aqueous solution of impure terephthalic acid and hydrogen in liquid phase, but also to prevent premature crystallization of the acid due to minor process variations causing vaporization of some of the solvent. This is readily accomplished by use of an inert, non-condensable gas such as nitrogen. By "inert" gas is meant that gas which is not reactive with the terephthalic acid or the hydrogen or solvent.

The hydrogenation process can be practiced using a suitable hydrogenation reactor arranged for intermittent introduction of hydrogen into a bed of catalyst during continuous introduction of the aqueous solution of impure terephthalic acid. The amount of hydrogen used is an excess of the amount required for reduction of the dissolved impurities. Although in practice very little hydrogen is consumed in the hydrogenation, i.e., purification, process, the amount of hydrogen used is in the range of from 1 to 7 moles excess above the stoichiometric amount required for the principle reducible impurities, 4-CBA and the characteristically yellow-colored impurities, while making allowance for other impurities of unknown structure. The nature of the end products of all of these impurities is not known but, by optical density measurement of the terephthalic acid product recovered after catalytic hydrogenation treatment, their absence or reduced concentration can be noted. Severe hydrogenation should be avoided so that conversion of terephthalic acid to such other products as cyclohexane, 1,4-dicarboxylic acid and p-toluic acid does not occur.

The hydrogenation catalyst is preferably a Group VIII Noble metal selected from platinum and/or palladium supported on adsorbent, high surface area charcoal. Reference may be made to any of the standard texts on hydrogenation or catalysts for materials which are catalytically effective under aqueous phase hydrogenation conditions.

The hydrogen treated aqueous solution can be filtered to remove any suspended solids, such as catalyst support fines and extraneous materials of about 5 microns and larger in size. The purified acid is then recovered from the filtered solution conveniently and preferably via crystallization, or via a series of crystallization steps in which the aqueous solution is cooled by releasing the pressure, which, in turn, vaporizes water and dissolved inert gas from the solution, and thereby causes pure terephthalic acid crystals to precipitate leaving pure plant mother liquor as the fluid medium. Following a predetermined number of crystallization steps, the slurry of pure terephthalic acid crystals is fed to a centrifuge, rotating drum filter or other suitable means for separating the pure acid crystals as a wet cake for further processing from the pure plant mother liquor. The pure plant mother liquor, which contains a residual amount of acetic acid along with some useful organic components as well as some dissolved impure terethphalic acid, is recycled for further use in the process. The present invention, in a second part, is directed to recovering this residual acetic acid from the pure plant mother liquor.

The invention in its fundamental embodiment comprises simultaneously introducing the second condensate from azeotropic distillation and the pure plant mother liquor which remains from the purification stage into a decanter coupled with sufficient mixing to thereby form an augmented aqueous phase and an organic phase across which the residual acetic acid, useful organic components and methyl acetate partition. The organic phase is then returned as reflux to the azeotropic tower wherein the residual acetic acid can be recovered and returned to the oxidation reaction, and the augmented aqueous phase is distilled to recover methyl acetate. In practice, satisfactory results are achieved when the second condensate from azeotropic distillation and the pure plant mother liquor are introduced into the decanter as a mixture. Satisfactory mixing is achieved by first passing the streams simultaneously through an in-line static mixer. A static mixer produces a controlled degree of mixing without creating an emulsion, although other mixing devices may also be used. A mixture of this type provides good extraction and sustainable downstream phase separation in the decanter.

According to an alternate and preferred embodiment of the invention, the second condensate (which results from condensing the tops product from the azeotropic tower) is separated into an organic phase comprising entrainer and an aqueous phase comprising water and methyl acetate. The aqueous phase is distilled to recover methyl acetate while the organic phase is preheated and then mixed with the pure plant mother liquor, and the resulting mixture is introduced into a second extraction decanter to thereby form an augmented aqueous phase and an organic phase across which the residual acetic acid, useful organic components and methyl acetate partition. The organic phase is then returned as reflux to the azeotropic tower wherein the residual acetic acid can be recovered and returned to the oxidation reaction, and the augmented aqueous phase is distilled to recover methyl acetate. In practice and as described above in connection with the fundamental embodiment of the invention, satisfactory results are achieved when the preheated organic phase from the first decanter and the pure plant mother liquor are introduced into the second extraction decanter as a mixture of the type which results from first passing the streams simultaneously through an in-line static mixer. A static mixer produces a controlled degree of mixing without creating an emulsion. A mixture of this type provides good extraction and sustainable downstream phase separation in the second extraction decanter. The organic phase from the first decanter is preheated to a temperature at, but usually above, the temperature of the incoming pure plant mother liquor, typically around 100° C., to avoid the possibility of precipitating solids when the two streams are mixed and introduced into the second extraction decanter. The temperature of the pure plant mother liquor is not critical and can vary over a broad range.

Turning now to the drawings, FIG. 1 is a simplified schematic flow diagram of one embodiment of the invention. It is to be understood that this embodiment is for the purpose of illustration and is not to be regarded as a limitation of the scope of the invention.

Referring to FIG. 1, pure terephthalic acid is produced commercially according to a two-stage process defined as comprising an oxidation stage 26 and a purification stage 12. Crude terephthalic acid is produced within oxidation stage 26 by air (molecular oxygen) oxidation of paraxylene in an acetic acid solvent using a metal bromide or other suitable catalyst system. The oxidation reaction generates a reactor overhead vapor stream which comprises water vapor, acetic acid, paraxylene, other minor components and an amount of methyl acetate which can range from 0.01% by wt. up to 5% by wt. Typically, the vapor stream will contain in the range of 69% w/w acetic acid, 12% w/w water and around 1% w/w methyl acetate, although these concentrations can vary over a broad range. Such variations will not materially affect the method of the invention. The vapor stream is withdrawn from the reactor, condensed and fed as a first condensate via line 1 to azeotropic distillation tower 14. Alternatively, a portion of the first condensate may be recycled to the oxidation reaction, in which case the other portion is fed via line 1 as shown to azeotropic distillation tower 14. Other water-rich feed streams, shown diagramatically as stream 2, can also be fed to azeotropic tower 14.

Crude terephthalic acid is recovered from oxidation stage 26 as a slurry which is then fed to a solvent exchange unit 16 via line 3. Solvent exchange unit 16 can be a centrifuge, a rotary drum filter or a moving belt filter, but typically solvent exchange will comprise a series of such units with a predetermined number of washing and re-slurry steps. In either case, the crude slurry is deposited as a wet cake onto a filter medium, and the medium moves the wet cake through sequential washing zones for washing with fresh water, recycled water or other suitable washing liquid introduced via line 5. Spent wash water, which now contains a substantial amount of acetic acid solvent, can be returned to oxidation stage 26, as shown, via line 4.

According to the embodiment shown in FIG. 1, water-washed crude terephthalic acid exits solvent exchange unit 16 as a wet cake via line 6 and passes to re-slurry tank 18. Alternatively, crude terephthalic acid can be supplied independently in dry form from storage. The crude terephthalic acid is re-slurried in water in re-slurry tank 18 and fed to purification stage 12 via line 7. The crude terephthalic acid dissolves in the aqueous solution when heated, and then impurities are selectively hydrogenated.

Azeotropic distillation is carried out in a suitable tower or column 14 in the presence of an organic entrainer, such as, for example, isopropyl acetate, n-butyl acetate and n-propyl acetate, which can form a low boiling two liquid phase azeotrope with water. The tops or overhead vapor product passes via line 8 to condenser 20, and a second condensate is recovered and fed via line 9 to decanter 22.

As described in greater detail above, pure terephthalic acid crystals are recovered via line 10 from purification stage 12 following catalytic hydrogenation of the solution of crude terephthalic acid at elevated pressure and temperature. After the pure terephthalic acid crystals are recovered leaving behind the pure plant mother liquor, the mother liquor, now at reduced pressure and a temperature in the range of 100° C., is fed via line 11 to decanter 22. Simultaneously mixing the pure plant mother liquor from the purification stage with the second condensate (line 9) from condenser 20 and introducing the mixture into decanter 22 results in augmenting the aqueous phase within the decanter and thereby extracting a larger portion of methyl acetate into the aqueous phase which is then fed via line 13 to organic distillation column 24. Residual acetic acid, which is present in the pure plant mother liquor, is simultaneously extracted in part in decanter 22 into the organic phase along with entrainer and acid precursors, and those components are returned to azeotropic tower 14 via line 15 as organic reflux. The bottoms product from azeotropic tower 14, shown as line 17, is around 95% by wt. acetic acid which can be returned to oxidation stage 26.

The aqueous phase from decanter 22 is fed via line 13 to organic distillation column 24 to remove volatile organic components and methyl acetate. Methyl acetate exits organic distillation column 24 as an overhead liquid or vapor stream, while water exits the base of the column via line 21. Intermediate organic components, such as residual entrainer, can be recycled to decanter 22 via line 23. Most notably, the water produced as a bottoms product via line 21 from the organic distillation column 24 can be combined with other waste water streams for effluent treatment or it can be recycled as appropriate for use in either solvent exchange via line 5, crude acid re-slurry via line 25 or for other uses.

Figure 2:
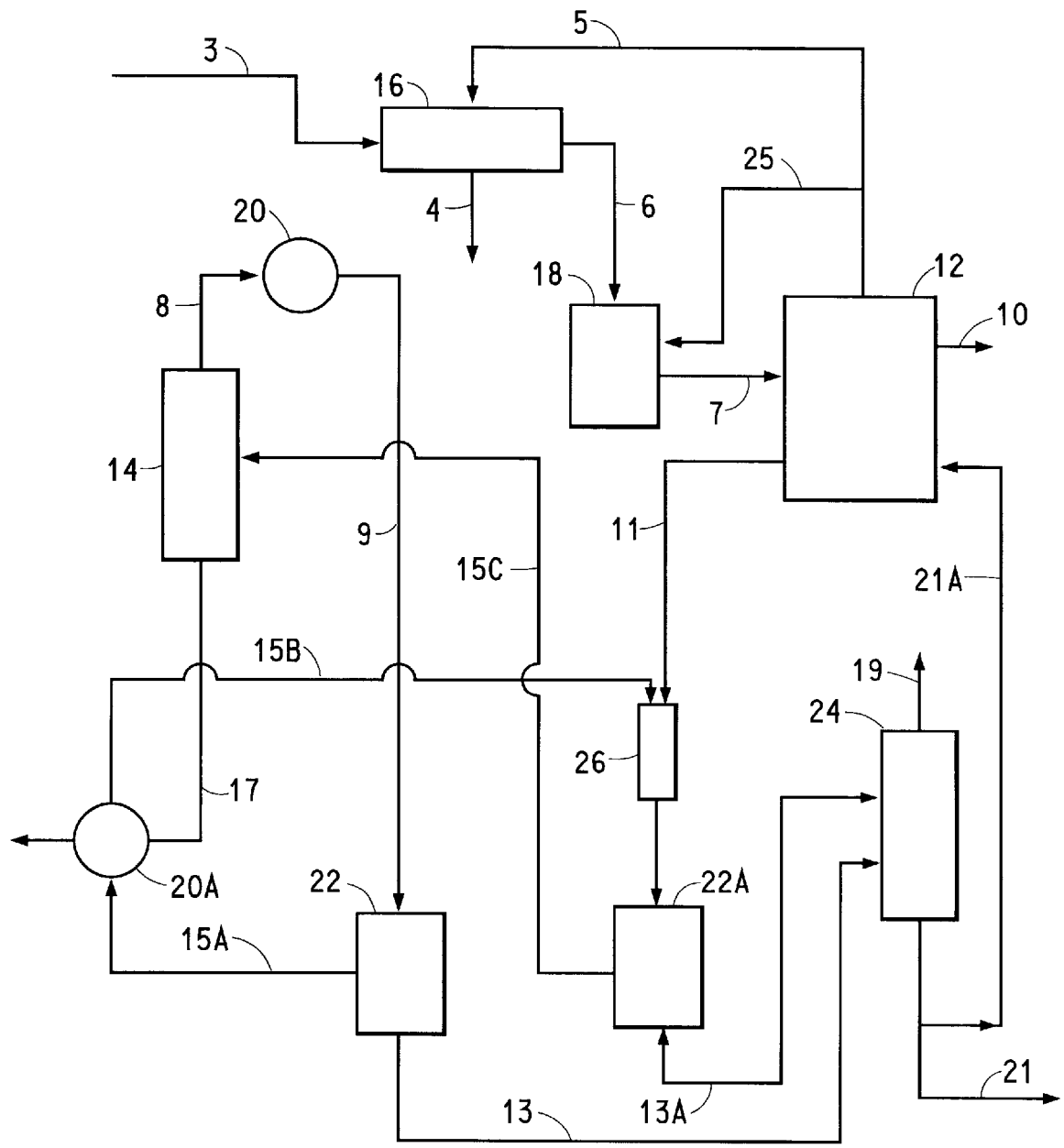
FIG. 2 is a schematic process diagram of an alternate embodiment for carrying out the method of the invention.

Referring now to FIG. 2, there is shown an alternate and preferred embodiment for carrying out the method of the invention according to which the second condensate (which results from condensing the tops product from the azeotropic tower) passes from condenser 20 via line 9 and is fed to decanter 22 where the second condensate is separated into an organic phase comprising entrainer and an aqueous phase comprising water and methyl acetate. The aqueous phase is fed via line 13 to organic distillation column 24. The organic phase comprising entrainer is passed via line 15A to extraction preheater 20A and then via line 15B to an in-line static mixer 26. The organic phase comprising entrainer (line 15B) and pure plant mother liquor (line 11) are fed simultaneously to a second extraction decanter 22A via static mixer 26, i.e., the incoming streams are introduced into extraction decanter 22A as a mixture without creating an emulsion which thereby provides a high level of extraction with sustainable downstream phase separation. The mixture forms an augmented aqueous phase and an organic phase across which residual acetic acid, useful organic components and methyl acetate partition. The organic phase is then returned via line 15C as reflux to the azeotropic tower wherein residual acetic acid can be recovered as a bottoms product and returned to oxidation stage 26, and the augmented aqueous phase is fed via line 13A to organic distillation column 24. A portion of the water produced as a bottoms product from the organic distillation column 24 can be recycled to purification stage 12 via line 21A as shown.

What is claimed is:

1. A method for recovering methyl acetate and residual acetic acid in a two-stage process for producing pure terephthalic acid according to a first oxidation stage and a second purification stage comprising:

(a) reacting paraxylene with air in the presence of acetic acid and a catalyst at elevated pressure and temperature to produce (1) an impure terephthalic acid which includes residual acetic acid and (2) a reaction off-gas stream comprising water, acetic acid and methyl acetate;

(b) cooling the reaction off-gas stream to form a first condensate and azeotropically dehydrating the first condensate in an azeotropic tower in the presence of an organic entrainer to produce a bottoms product comprising acetic acid and a tops product and cooling the tops product to form a second condensate comprising water, methyl acetate and organic entrainer;

(c) purifying the crude terephthalic acid by dissolving it in water at elevated pressure and temperature to form an aqueous solution and contacting the aqueous solution with hydrogen in the presence of a catalyst;

(d) adjusting the pressure and temperature of the hydrogenated aqueous solution whereby pure terephthalic acid crystals precipitate and residual acetic acid and organic components remain in solution to form pure plant mother liquor; wherein the method comprises:

(e) simultaneously introducing the second condensate and the pure plant mother liquor into a decanter to form an aqueous phase and an organic phase across which residual acetic acid, organic components and methyl acetate partition; and (f) returning the organic phase to the azeotropic tower to recover residual acetic acid and distilling the aqueous phase to recover methyl acetate.

2. The method of claim 1 in which simultaneously introducing the second condensate and the pure plant mother liquor into said decanter comprises passing the second condensate and the pure plant mother liquor concurrently through a static mixer first and then introducing the mixture into the decanter.

3. A method for recovering methyl acetate and residual acetic acid in a two-stage process for producing pure terephthalic acid according to a first oxidation stage and a second purification stage comprising:

(a) reacting paraxylene with air in the presence of acetic acid and a catalyst at elevated pressure and temperature to produce (1) an impure terephthalic acid which includes residual acetic acid and (2) a reaction off-gas stream comprising water, acetic acid and methyl acetate;

(b) cooling the reaction off-gas stream to form a first condensate and azeotropically dehydrating the first condensate in an azeotropic tower in the presence of an organic entrainer to produce a bottoms product comprising acetic acid and a tops product and cooling the tops product to form a second condensate comprising water, methyl acetate and organic entrainer;

(c) purifying the crude terephthalic acid by dissolving it in water at elevated pressure and temperature to form an aqueous solution and contacting the aqueous solution with hydrogen in the presence of a catalyst;

(d) adjusting the pressure and temperature of the hydrogenated aqueous solution whereby pure terephthalic acid crystals precipitate and residual acetic acid and organic components remain in solution to form pure plant mother liquor; wherein the method comprises:

(e) separating the second condensate into an aqueous phase comprising water and acetic acid and an organic phase comprising entrainer;

(f) simultaneously introducing the organic phase and the pure plant mother liquor into a decanter to form an aqueous phase and an entrainer-rich organic phase across which acetic acid, organic components and methyl acetate partition; and (g) returning the organic phase to the azeotropic tower to recover residual acetic acid and distilling the aqueous phases from step (e) and step (f) to recover methyl acetate.

4. The method of claim 3 which further comprises mixing the organic phase from step (e) and the pure plant mother liquor first and then introducing the resulting mixture into a decanter according to step (f).

* * * * *